United States Patent [19]

Lui et al.

[11] Patent Number: 4,638,028

[45] Date of Patent: Jan. 20, 1987

[54] RUBBER POLYMERASES AND METHODS FOR THEIR PRODUCTION AND USE

[75] Inventors: Joseph H. Lui, Akron; David S. Shreve, Mogadore, both of Ohio

[73] Assignee: Goodyear Tire & Rubber Company, Akron, Ohio

[21] Appl. No.: 720,740

[22] Filed: Apr. 8, 1985

[51] Int. Cl.$^4$ ............................................. C08K 5/05
[52] U.S. Cl. ................................. 524/387; 435/167; 435/166; 435/183; 435/814; 435/815; 435/816; 523/122; 524/386; 524/428
[58] Field of Search ............... 523/122; 524/377, 386, 524/387, 388, 428; 435/166, 167, 183, 814, 815, 816

[56] References Cited

U.S. PATENT DOCUMENTS 3,214,398  10/1965  Vannoy ............................. 523/122
3,442,845   5/1969  Columbus .......................... 524/388
4,055,529  10/1977  Burley ............................... 524/388
4,472,540   9/1984  Barker .............................. 524/388

OTHER PUBLICATIONS

Berndt, J., The Biosynthesis of Rubber (Max-Planck-Institut fur Zellchemie, Munich, Federal Republic of Germany), 1963.

Park, R. B. and J. Bonner, *J. Biol. Chem.*, 223:340–343, 1958.
Benedict et al., *Plant Physiol.*, 72:897–899, 1983.
Archer, B. L. and E. G. Cockbain, Methods in Enzymology, 15:476–480, 1969.
Agranoff et al., *The Journal of Biological Chemistry*, 235:326–332, 1960.
Archer, B. L. and B. G. Audley, Advances in Enzymology, 29:221–257, 1967.
Lynen, F., *J. Rubber Res. Inst. Malaya*, 21(4):389–406, 1969.

*Primary Examiner*—Paul R. Michl
*Attorney, Agent, or Firm*—Finnegan, Henderson, Farabow, Garrett & Dunner

[57] ABSTRACT

Substantially pure rubber polymerase and analogues thereof are disclosed. Substantially pure rubber polymerase is isolated and purified from chemically stabilized *Hevea brasiliensis* latex. The analogues exhibit substantial homology to the *Hevea brasiliensis* polymerase or function in an enzymatically equivalent manner. Methods for the isolation and purification of a rubber polymerase are set forth. Use of substantially pure rubber polymerase to produce natural rubber or related copolymers is also disclosed.

7 Claims, No Drawings

RUBBER POLYMERASES AND METHODS FOR THEIR PRODUCTION AND USE

BACKGROUND OF THE INVENTION

This invention relates to rubber polymerases in substantially pure form and methods for their production and use in the in vitro synthesis of natural rubber, particularly high molecular weight natural rubber.

Natural rubber is found in thousands of plants from various families. Several fungi have also been reported to synthesize natural rubber. Most plants and all of the fungi contain very little rubber, and the molecular weight of the rubber is too low for the rubber to be of commercial value.

The two sources of natural rubber that have been used commercially are *Hevea brasiliensis* and *Parthenium argentatum* (guayule). *H. brasiliensis* is the dominant source of natural rubber. Guayule was a commercial source of natural rubber in the first part of this century, providing 10% of the world supply in 1910. During World War II, when the United States' supply of natural rubber from Southeast Asia was cut off, a large-scale planting of guayule was conducted by the U.S. Forest Service as part of the Emergency Rubber Project. When the war was over, the low price and high availability of *H. brasiliensis* rubber made guayule an unattractive source of natural rubber. The dominance of *H. brasiliensis* continues today. However, recent economic and political trends encourage the development of alternative sources of high molecular weight natural rubber. One of these sources is in vitro synthesis.

The pathway of rubber biosynthesis in *H. brasiliensis* is well established and has been reviewed by Archer and Audley, *Advances in Enzymology*, 29: 221–257, 1967 and Lynen, *J. Rubber Res. Inst. Malaya*, 21(4): 389–406, 1969. The final step in the biosynthesis of rubber is catalyzed by the enzyme rubber polymerase, which is found in the latex. This enzyme catalyzes the polymerization of isopentenyl pyrohosphate (IPP) onto an allylic pyrophosphate to make rubber with the production of inorganic pyrophosphate. The enzyme has also been called rubber transferase or cis-1,4-polyisoprene pyrophosphate: isopentenyl pyrophosphate cis-1,4-polyisoprenyl transferase. It is a member of the group of enzymes called prenyltransferases, which polymerize IPP to different chain lengths and stereochemical configurations. The term "rubber polymerase" will be used herein to describe the enzyme.

In *H. brasiliensis* latex, the enzyme is mainly associated with rubber particles, but it is also found free in solution, Archer and Audley, supra. The synthesis of rubber takes place on the surface of the rubber particles, Lynen, supra. Even though studies of rubber polymerase have been carried out in a number of laboratories (Archer and Audley, supra; Lynen, supra; Archer and Cockbain, *Methods in Enzymology*, 15: 476–481, 1969), successful production of rubber polymerase from *H. brasiliensis* or any other source in substantially pure form has not been achieved prior to the present invention.

Rubber polymerase in substantially pure form will have several applications that will be very important for the rubber industry. The enzyme, either immobilized or free in solution, could be used to produce natural rubber in vitro. This would allow the production of the rubber without the use of *H. brasiliensis* latex and at locations near factories where the rubber is processed into finished articles, such as tires. In addition, natural rubber made in vitro may even be superior to natural rubber produced from *H. brasiliensis* latex because the conditions for making natural rubber in vitro could be controlled so as to produce natural rubber of higher purity or having other desirable chemical or physical properties. For example, the in vitro rubber would be more uniform and would also be substantially free of proteins and lipids that can interfere with certain applications of natural rubber.

Another important application would to prepare antibodies to the substantially pure rubber polymerase. Such antibodies could be used to develop a screening method for plants and other organisms to determine the amount of rubber polymerase in such organisms.

In still another important application, the purified enzyme could be sequenced and, using the sequence of the enzyme, the rubber polymerase gene or a probe for the gene could be synthesized. Once the gene for the enzyme was identified, the ability to produce natural rubber could be introduced into other organisms. Finally, once more is known about the sequence and structure of the enzyme, site directed mutagensis could be used to produce a rubber polymerase with altered catalytic properties. This would allow more control over the biosynthesis of natural rubber in vivo and in vitro.

SUMMARY OF THE INVENTION

An object of the present invention is to provide substantially pure rubber polymerases and active analogues of such polymerases with equivalent or enhanced properties.

An additional object of the present invention is to provide processes for the isolation and purification of rubber polymerase.

Another object of the present invention is to provide a process for using substantially pure rubber polymerase to produce natural rubber, particularly high molecular weight natural rubber, or to produce copolymers.

Still another object of the present invention is to provide a process for the preparation of a material used in the process of producing natural rubber, particularly high molecular weight natural rubber.

To achieve the objects and in accordance with the purpose of the present invention, rubber polymerase in substantially pure form is disclosed. In one preferred embodiment, rubber polymerase is recovered in substantially pure form from *Hevea brasiliensis* latex. In another embodiment, the active analogues are provided, which are substantially pure polypeptides having at least one active site with rubber polymerase activity, which site may exhibit substantial homology to the rubber polymerase recovered from *Hevea brasiliensis* latex or may function in a manner enzymatically equivalent to such polymerase recovered from *Hevea brasiliensis* latex. In still another embodiment, the active site is altered to form a polypeptide having enhanced rubber polymerase activity. In accordance with an especially preferred embodiment of the present invention, the rubber polymerase is monomeric and has a molecular weight from about 36,000 to about 44,000, as determined by sodium dodecyl sulfate polyacrylamide gel electrophoresis.

In accordance with the present invention, there is provided a process for producing rubber polymerase in substantially pure form by preparing chemically stabilized latex from a plant of the genus Hevea which contains rubber polymerase bound to rubber particles in the latex and rubber polymerase free in solution, separating the rubber polymerase free in solution from the latex, and purifying the separated rubber polymerase. Chemically stabilized latex is prepared by adding to the latex a stabilizing composition comprising a polyhydroxy compound, an antimicrobial agent, and a buffer. In a preferred embodiment, the stabilizing composition further comprises a sulfhydryl compound.

Rubber polymerase free in solution is separated from the latex by chromatography. Ion exchange chromatography is preferred.

In a preferred embodiment, the rubber polymerase is purified by dialyzing the separated rubber polymerase to produce ia dialysate, adding a gel to the dialysate to form a gel-polymerase complex, separating the complex, removing the polymerase from the complex, and subjecting the removed polymerase to gel filtration chromatography to produce rubber polymerase in substantially pure form.

In another preferred embodiment, the polymerase is separated and purified by bringing the the chemically stabilized latex into contact with immobilized antibodies to a rubber polymerase so as to form a rubber polymerase-antibody complex, separating the complex, and recovering the rubber polymerase from the complex. In an alternative embodiment, the rubber polymerase is purified by bringing the rubber polymerase free in solution into contact with immobilized antibodies to a rubber polymerase so as to form a rubber polymerase-antibody complex, separating the complex, and recovering the rubber polymerase from the complex.

This invention also provides a process for producing natural rubber by forming a reaction mixture containing isopentenyl pyrophosphate, an allylic pyrophosphate, and substantially pure rubber polymerase; incubating the reaction mixture for a time sufficient to produce the natural rubber; and recovering the natural rubber. In a preferred embodiment, high molecular weight natural rubber is produced.

In an alternative embodiment, a process is provided for producing a copolymer by forming a reaction mixture containing isopentenyl pyrophosphate and at least one other copolymerizable monomer, an allylic pyrophosphate, and substantially pure rubber polymerase; incubating the reaction mixture for a time sufficient to produce a copolymer; and recovering the copolymer.

This invention also relates to a process for the preparation of dimethylallyl pyrophosphate by forming a reaction mixture containing isopentenyl pyrophosphate, isopentenyl pyrophosphate isomerase, a divalent metallic ion, a phosphatase inhibitor, and a buffer; incubating the reaction mixture for a time sufficient to produce the dimethylallyl pyrophosphate; and recovering the dimethylallyl pyrophosphate.

Additional objects and advantages of the invention will be set forth in part in the description that follows and in part will be obvious from the description or may be learned from practice of the invention. The objects and advantages may be realized and obtained by means of the instrumentalities and combinations particularly pointed out in the appended claims.

DETAILED DESCRIPTION OF THE INVENTION

Reference will now be made in detail to the presently preferred embodiments of the invention, which, together with the following examples, serve to explain the principles of the invention.

The present invention relates to rubber polymerases, particularly those that have been isolated and produced in substantially pure form. As used herein, the term "rubber polymerase" is intended to mean a polypeptide that catalyzes the formation of natural rubber (cis-1,4-polyisoprene) from isopentenyl pyrophosphate (IPP) and an allylic pyrophosphate. The terms "substantially pure" and "substantially purified", when used to refer to the rubber polymerases disclosed herein, shall mean rubber polymerases substantially free of proteins or polypeptides that are not rubber polymerases. The substantially pure rubber polymerases of the present invention are at least 75%, preferably 85%, and most preferably at least 90% pure by weight. That is, the substantially pure rubber polymerases of the present invention contain no more than 25%, preferably no more than 15%, and most preferably no more than 10% by weight proteins or polypeptides that are not rubber polymerases.

In a preferred embodiment, the rubber polymerase of the present invention is recovered from *Hevea brasiliensis* latex. It has a subunit molecular weight from about 36,000 to about 44,000, as determined by sodium dodecyl sulfate polyacrylamide gel electrophoresis. The active form of the enzyme is monomeric as determined by gel filtration chromatography.

The rubber polymerases of the present invention may be produced in substantially pure form by the following method:

(a) preparing chemically stabilized latex from a plant of the genus Hevea;

(b) separating the rubber polymerase that is free in solution from the latex; and (c) purifying the separated rubber polymerase.

The purification of the rubber polymerase requires a source of large quantities of latex. During shipment, the latex should be stabilized to prevent coagulation and fermention, which cause a loss of activity of the polymerase. Conventionally, such stabilization has been accomplished by chilling or freezing the latex. However, this is a cumbersome and costly procedure. The present invention provides a means for chemically stabilizing the latex to allow it to be shipped at ambient temperature. Latex stabilized in this manner shows few, if any, signs of coagulation or fermentation for at least 10 days, and it retains a high level of active rubber polymerase.

The process for stabilizing the latex comprises adding a stabilizing composition to the latex. The stabilizing composition comprises a polyhydroxy compound, an antimicrobial agent, and a buffer. In a preferred embodiment, the stabilizing composition also contains a sulfhydryl compound such as cysteine or glutathione, which helps to stabilize the polymerase. In a particularly preferred embodiment, the stabilizing composition is a solution. From about one to about 10 volumes, preferably approximately two volumes, of stabilizing solution, are mixed into approximately one volume of latex.

Preferred polyhydroxy compounds include glycerol, sorbitol, sucrose and the like. Glycerol is particularly preferred. The polyhydroxy compound appears to stabilize the rubber polymerase and also to prevent coagulation of the rubber particles in the latex, which appears to trap or otherwise inactivate the rubber polymerase.

The antimicrobial agent also aids in preventing coagulation and fermentation. A preferred antimicrobial agent is sodium azide.

The buffer prevents extremes in pH, which can inactivate the enzyme. The choice of the buffer is not critical, although sodium bicarbonate or potassium phosphate have been found to be particularly useful. In particular, 0.1 M sodium bicarbonate or 0.1 M potassium phosphate is preferred.

In a preferred embodiment, the stabilizing solution is comprised of from about 10% to about 80% weight/volume glycerol, from about 0.001% to about 1% weight/volume sodium azide, and approximately 0.1 M sodium bicarbonate. The pH of the sodium bicarbonate is adjusted so that the solution containing the stabilizing mixture has a pH from about 7 to about 12 and preferably about 8. In a particularly preferred embodiment, the stabilizing solution is composed of approximately 50% weight/volume glycerol, approximately 0.3% weight/volume sodium azide, approximately 0.1 M sodium bicarbonate, and approximately 5 mM cysteine.

Approximately 10-20% of the rubber polymerase in *H. brasiliensis* latex, stabilized as described above, is free in solution. The remainder of the enzyme is tightly bound to the rubber particles in the latex. Bound enzyme is extremely difficult to separate from the rubber particles without inactivating the enzyme. The present invention makes it possible to isolate and substantially purify the rubber polymerase, which is free in solution, while retaining its activity.

The free rubber polymerase may be separated from the latex by separation techniques generally well-known in the art, which may be adapted to the present invention by those of ordinary skill in the art in light of the teachings of the present specification. Chromatography is particularly preferred. In particular, ion exchange chromatography, employing an anion exchange resin, is used. The preferred resin is diethylaminoethyl (DEAE) cellulose. The resin is mixed into the latex so that the free rubber polymerase binds to the resin. The resin is then removed by centrifugation and washed. The enzyme is eluted from the resin by techniques well-known in the art. Some rubber particles, which are bound to the resin, are also eluted. These may be separated from the enzyme by ultracentrifugation and discarded. Although the separation procedure may be conducted at a temperature from about 0° C. to about 30° C., it is preferred that it be conducted at a temperature from about 0° C. to about 4° C.

At this point, the enzyme is only partially purified. It may be further purified by techniques generally well-known in the art, which may be adapted to the present invention by those of ordinary skill in the art in light of the teachings of the present specification. Such techniques include chromatography (including affinity chromatography, ion exchange chromatography, size exclusion chromatography, and adsorption chromatography), precipitation, dialysis, centrifugation, electrophoresis, isoelectric focusing, and variations and combinations thereof. One or more of these techniques are employed sequentially in a procedure designed to separate molecules according to their physical and chemical characteristics. These characteristics include the hydrophobicity, charge, and molecular weight of the rubber polymerase. The various fractions of materials obtained after each technique are tested for their ability to catalyze the formation of high molecular weight natural rubber. One of these tests is described in Lynen, *J. Rubber Res. Inst. Malaya*, 21(4): 389–406, 1969, which is incorporated herein by reference. Those fractions showing rubber polymerase activity are then subjected to the next technique in the sequential procedure, and the new fractions are tested again. The process is repeated until only one fraction having the ability to catalyze the formation of natural rubber remains and that fraction contains at least 75%, preferably 85%, and most preferably 90% active rubber polymerase by weight. Although the purification steps may be conducted at a temperature from about 0° C. to about 30° C., it is preferred that they be conducted at a temperature from about 0° C. to about 4° C.

In a preferred embodiment, the partially purifed rubber polymerase, recovered from the ion exchange resin, is dialyzed through a cellulose membrane designed to remove all material of a molecular weight less than 12,000-14,000. The dialysis medium is a standard buffer solution with a pH of approximately 5.5–6.7, with a pH of approximately 6.2 being preferred. Such dialysis decreases the ionic strength of the solution and also lowers its pH to approximately 6.2 by removing salts and stabilizing agents. It also appears to remove inhibitors of the enzyme. Other techniques known in the art that accomplish the same purposes may be used. Decreasing the ionic strength of the solution appears to be important to the efficient purification of the enzyme.

The dialysate is then mixed with an adsorbent for proteins or polypeptides, such as alumina C gamma, for approximately 1 hour. The adsorbent appears to remove inhibitors of the polymerase; however, it's use is believed not to be critical to its purification. It is removed by centrifugation.

The supernatant, which contains the rubber polymerase, is then mixed with a 0.1-10 volume of a gel, such as calcium phosphate, which forms a complex with the enzyme. The mixture is stirred from approximately 1-100 minutes, with 30 minutes being preferred. It is desirable to let the mixture sit for about 10-100 minutes, preferably 50 minutes. The complex is then removed by centrifugation and the supernatent is discarded. The complex is then washed with a buffer, and the enzyme is eluted. At this point, the eluted material produces approximately 2 or 3 major bands and several minor bands when subjected to sodium dodecyl sulfate polyacrylamide gel electrophoresis.

The eluted material is then subjected to gel filtration chromatography. A substantially pure rubber polymerase is produced which is most preferably at least 90% pure by weight. If desired, the substantially pure rubber polymerase can be further purified by chromatography. In particular, affinity chromatography or ion exchange chromatography is preferred.

The substantial purification of rubber polymerase allows the production of antibodies to the enzyme. Antibodies are highly specific and have high affinities for the polypeptides they have been raised against. When attached to an insoluble matrix, they allow the easy and efficient separation of the polypeptide they have been raised against from a complex mixture of proteinaceous and other substances. The immobilized antibodies are brought into contact with the mixture, allowing the rubber polymerase to bind to the antibodies. The mixture is then removed and the insoluble matrix containing the polymerase bound to the antibodies is washed to remove additional traces of the mixture. The polymerase may then be separated and eluted from the antibodies. The methods of using antibodies in this fashion are well-known in the art and disclosed in R. Scopes, *Protein Purification: Principles and Practice* (New York: Springer Verlag, 1982), pgs. 132–136, which is incorporated herein by reference.

In the present invention, the rubber polymerase free in solution after separation from the chemically stabilized latex is brought into contact with immobilized antibodies to a rubber polymerase so that polymerase-antibody complexes are formed. These complexes are separated from the solution, and the polymerase is eluted in substantially pure form from the complexes. Alternatively, the chemically stabilized latex itself can be brought into contact with the immobilized antibodies, forming polymerase-antibody complexes. These complexes are then separated from the latex. Some of the polymerase-antibody complexes may also be bound to rubber particles, and when the enzyme is eluted some of the enzyme may be bound to rubber particles. The rubber particles with bound enzyme may be separated by centrifugation, leaving substantially purified rubber polymerase in solution.

Antibodies to rubber polymerases may be made by various techniques well-known in the art. Polyclonal antibodies may be made by injecting rubber polymerase into rabbits, goats, horses, or other animals. The animals are then bled, and the presence of antibodies can be determined by such methods as double diffusion or detection of antibody-antigen aggregrates using $^{125}$I-labeled protein A. The antibodies to the polymerase are recovered from the serum. Generally, it is necessary only to partially purify the antibodies. In an alternative embodiment, monoclonal antibodies may be used instead of polyclonal antibodies, and, in fact, they would be preferable when working with only a partially purified mixture containing rubber polymerase and other polypeptides. Monoclonal antibodies may be prepared using the technique of Kohler and Milstein, *Nature*, 256: 495, 1975, which is incorporated herein by reference.

The antibodies need not be made by using as the antigen the particular rubber polymerase sought to be recovered or produced. If rubber polymerases made by different types of plants are identical or substantially similar to each other, an antibody to one such polymerase would be expected to bind to the rubber polymerase from a different rubber producing plant. Thus, the combination of well-known techniques for using antibodies to purify proteinaceous materials with the teachings of this invention for the production of substantially pure rubber polymerase from plants of the genus Hevea would allow any organism to be tested for its ability to produce rubber polymerase and, if such ability were found, would allow the isolation and purification of such polymerase.

Various techniques may be used to immobilize the antibodies and then bring them into contact with the mixture that contains the rubber polymerase. The technique of immunoadsorbent affinity chromatography is preferred. In this technique, the antibodies are coupled to an adsorbent, such as cyanogen-bromide activated agarose, in a column. Mixtures are run through the column at a rate slow enough so that the rubber polymerase can fully interact the immobilized antibodies. The column may be washed and then eluted to remove the polymerase from the antibodies. Detergents or other buffers may be used to elute the polymerase.

As previously mentioned, natural rubber is found in many different species of plants. *H. brasiliensis,* the preferred commercial source of natural rubber, is one of approximately nine species of the genus Hevea. Although the biosynthesis of rubber in the other species has not been as well studied as in the case of *H. brasiliensis,* it is to be expected that the other species contain rubber polymerase identical or substantially similar to the polymerase isolated and purified from *H. brasiliensis.* Similarly, the rubber polymerase found in guayule would be expected to be identical or substantially similar to that from *H. brasiliensis.* Such polymerases are enzymatically equivalent to the rubber polymerase found in *H. brasiliensis* latex. That is, they catalyze the synthesis of natural rubber from IPP and an allylic pyrophosphate. Therefore, the teachings of the present invention can be applied to the isolation and purification of rubber polymerase from other plants that produce natural rubber, and such polymerases are within the scope of the present invention.

It is also within the scope of the present invention to provide a class of rubber polymerases having common elements of structure and mechanism of action and different from one another in only a relatively few amino acid residues. In addition to being isolated from different plants, members of such class can be produced by chemical modification or genetic modification, such as site directed mutagensis, of existing members by techniques well-known in the art once such members are identified and isolated by antibodies prepared to the rubber polymerase of the present invention purified from *Hevea brasiliensis* latex. The chemical modifications may enhance the activity of the original polymerase or may have no effect on such activity. In addition, the present invention allows the cloning of the gene coding for the active rubber polymerase. Once this gene is cloned, numerous modifications of the active material can be made by base substitution and introduction of the modified gene into a variety of hosts.

It is also contemplated that the rubber polymerases of the present invention may contain one or more amino acid sequences that are not necessary to their activity. Such sequences can be removed by techniques well-known in the art. For example, unnecessary amino acid sequences could be readily removed by a limited proteolytic digestion using enzymes such as trypsin or papain or related proteolytic enzymes. Thus, such rubber polymerases are within the scope of the present invention.

The rubber polymerases of the present invention may be used to produce natural rubber of any desired molecular weight within the range of approximately 1,000–2,000,000. Such rubber may be produced by forming a reaction mixture containing isopentenyl pyrophosphate, an allylic pyrophosphate, and purified or substantially purified rubber polymerase; incubating the reaction mixture for a time sufficient to produce natural rubber; and recovering the rubber. The use of the purified or substantially purified rubber polymerase of the present invention may be expected to limit competing reactions. This would provide a less contaminated product, which is easier and cheaper to purify further.

The allylic pyrophosphate can be low or high molecular weight natural rubber particles or an initiator such as dimethylallyl pyrophosphate (DMAPP). When low molecular weight natural rubber is used, the process converts such low molecular weight natural rubber into higher molecular weight natural rubber. It is particularly preferable to use both DMAPP and natural rubber particles in the reaction. The molecular weight of the natural rubber produced in vitro can be controlled by varying the reaction time, the ratio of IPP to allylic pyrophosphate, the molecular weight of allylic pyrophosphate, and combinations thereof. In a preferred embodiment, 2–10 mM IPP, 3–50 uM DMAPP, 0.1–1% (weight/volume) rubber particles, and 0.1–1% (weight/volume) of substantially pure polymerase are used to produce high molecular weight natural rubber.

In a preferred embodiment, the reaction mixture also contains a divalent metallic ion, a heavy metal chelating agent, an enzyme stabilizing agent, and a buffer. A preferred source of the divalent metallic ion is magnesium chloride. Although the divalent metallic ion appears to be necessary for the reaction, trace amounts of ions such as $Mg^{++}$ are found in most of the other reagents. Therefore, it does not appear to be essential to add magnesium chloride or similar compounds to the reaction mixture. The concentration of the magnesium chloride in the reaction mixture can range from 0 to 100 mM. When used, the concentration can range from 0.01 to 100 mM. The preferred concentration is 1–10 mM.

The heavy metal chelating agent appears to be a protecting agent for the polymerase, but it does not apear to be critical to the reaction. Dipotassium ethylenediaminetetraacetate (EDTA) is particularly preferred. Its concentration can range from 0 to 100 mM. When used, the concentration can range from 0.01 to 100 mM. The preferred concentration is 5–10 mM.

Sulfhydryl compounds, such as cysteine and glutathione, also appear to be protecting agents for the polymerase, but they are not critical to the reaction. Glutathione is particularly preferred. Its concentration can range from 0–100 mM. When used, the concentration can range from 0.01 to 100 mM. The preferred concentration is 1–10 mM.

The reaction can be carried out at a pH of about 5 to about 10 with the preferred pH being from about 7 to about 8. The pH is controlled by the buffer, and many different buffers are satisfactory. It is preferred that Tris (Tris(hydroxymethyl) nitromethane) buffer be used. Its concentration can range from 1 mM–10 M. The optimum concentration is 0.1 M–1.6 M.

The reaction may be carried out a temperature from about 4° C. to about 60° C. for about 1 to about 16 hours. It is preferred that the temperature be approximately 30° C. and the reaction time be approximately 4–8 hours.

DMAPP may be prepared by forming a reaction mixture containing isopentenyl pyrophosphate, isopentenyl pyrophosphate isomerase, a divalent metallic ion, a phosphatase inhibitor, and a buffer; incubating the reaction mixture; and recovering the DMAPP. The DMAPP may be recovered by filtering the mixture through a membrane with a 10,000 molecular weight cutoff. The DMAPP is in the filtrate. It is preferred that the reaction mixture be incubated for approximately 1–2 hours at a temperature of approximately 35°–40° C., preferably 37° C. A preferred divalent metallic ion is $Mg++$ and the preferred phosphatase inhibitor is sodium fluoride. An acceptable buffer is sodium bicarbonate. The IPP isomerase is prepared by techniques known in the art. One such technique is that disclosed in Agranoff, et al., *The Journal of Biological Chemistry*, 235: 326–332, 1960, which is incorporated herein by references.

In an alternative embodiment, the purified or substantially purified rubber polymerase may be used to produce a copolymer from IPP and at least one other copolymerizable monomer and an allylic pyrophosphate under conditions similar to the process for making natural rubber. Suitable copolymers include butadiene, styrene, acrylonitrile, and vinyl. The molecular weight of the copolymer can be controlled by varying the reaction time, the ratio of IPP to allylic pyrophosphate, the molecular weight of the allylic pyrophosphate, the amount of copolymerizable monomer, and combinations thereof.

The natural rubber produced by the process of the present invention may be assayed by techniques well-known in the art. In particular, such techniques include ozonolysis (Park and Bonner, *J. Biol. Chem.*, 233: 341–343, 1958, incorporated herein by reference), reverse phase thin layer chromatography (Bui and Armstrong, *J. Liquid Chromatography*, 7: 29, 1984, incorporated herein by reference) and solvent extraction (Benedict, et al., *Plant Physiol.*, 72: 897–899, 1983, incorporated herein by reference).

It is to be understood that the applicant of the teachings of the present invention to a specific problem or environment will be within the capabilities of one having ordinary skill in the art in light of the teachings contained herein. Examples of the products of the present invention, processes for their production, and processes for their use appear in the following examples.

EXAMPLE I

Stabilization of *H. brasiliensis* Latex and Rubber Polymerase

The stabilization mixture was prepared as follows. One thousand (1,000) grams of glycerol were mixed with 1.2 l of distilled water. To this mixture were added 16 grams of sodium bicarbonate, 6 grams of sodium azide, and 2 grams of cysteine. The volume of the final solution was approximately 2 liters and contained 50% (weight/volume) glycerol, 0.3% (weight/volume) sodium azide, 5 mM cysteine, and 0.1 M sodium bicarbonate. Two liters of the stabilization solution were mixed thoroughly with one liter of latex (30% by weight dry solids) immediately after the latex was collected from *H. brasiliensis* trees.

EXAMPLE II

Separation of Rubber Polymerase from Latex

DEAE cellulose was equilibrated with 67 mM NaHCO$_3$, 33% (v/v) glycerol, and 3 mM cysteine. All steps in the isolation of the rubber polymerase that is free in solution were performed at 0°–4° C. The latex and DEAE cellulose were incubated together for 1 hour. The DEAE cellulose was then isolated by centrifugation at 16,000×g for 10 minutes. The DEAE cellulose was then resuspended in 0.3 l of the same buffer solution as that used to equilibrate the DEAE cellulose and centrifuged as above. The rubber polymerase bound to the DEAE cellulose was eluted by washing the DEAE cellulose with 0.4 M NaCl in the buffer solution used to equilibrate the DEAE cellulose. The eluted enzyme contained rubber particles that were physically or electrostatically trapped by the DEAE cellulose, but the majority of the rubber polymerase was free in solution. Subsequent ultracentrifugation at 235,000×g for 1 hour removed the rubber from the solution and left most of the active rubber polymerase in the solution.

EXAMPLE III

Separation of Rubber Polymerase from Latex

An alternative procedure for the treatment of latex with DEAE cellulose was devised. The latex was first centrifugated at 28,000×g for 1 hour. Some of the rubber in the latex layered out on top of the solution. The solution was then treated with DEAE cellulose as described above except that the DEAE cellulose was separated from the solution at each washing or elution step by vacuum filtration. Centrifugation was used to isolate the DEAE cellulose from uncentrifuged latex, since the rubber in the latex prohibited efficient filtration of the DEAE-latex mixture.

The rubber polymerase that was eluted from the DEAE cellulose still contained rubber. This was removed by centrifugation at 235,000×g for 1 hour. A clear solution that contained a significant amount of active rubber polymerase was produced.

EXAMPLE IV

Purification of Rubber Polymerase

Rubber polymerase free in solution, produced as in Example II, was purified to near homogeneity. All steps during the purification of the enzyme were performed at 0°–4° C.

A clear solution of rubber polymerase produced as described in Example II was dialyzed overnight against 15 l of 1 mM 2(N-morpholino)ethanesulfonic acid, pH 6.2. The protein concentration in the dialyzed enzyme was determined by the method of Warburg and Christian, *Biochemical Zeitschrift*, 24: 206, 1931, incorporated herein by reference. One half (0.5) gram of 16 mg/ml alumina C gamma (Sigma Chemical Company) per gram of protein was added to the solution and incubated for 1 hour. The alumina C gamma was removed from the solution by centrifugation at 10,000×g for 5 minutes. The rubber polymerase did not bind to the alumina C gamma.

Calcium phosphate gel was prepared as described by Tsuboi and Hudson, *J. Bio. Chem.*, 224: 879, 1957, incorporated herein by reference. The enzyme that had been treated with alumina C gamma was mixed with an equal volume of calcium phosphate gel (10 mg/ml). The mixture was stirred for 30 minutes and let sit for 50 minutes. The gel was re-suspended in 30 ml of the buffer used to equilibrate the DEAE (Example II) by blending in a blender at low speed for 1 minute. The mixture was then allowed to sit for 50 minutes before the gel was isolated again. The enzyme was then eluted from the gel by blending with 30–100 ml of 0.2 M $K_2HPO_4$, glycerol 33% (w/v), and 3 mM 2-mercaptoethanol.

The enzyme eluted from the calcium phosphate gel was further purified by gel filtration using Ultrogel AcA44 (LKB Instruments, Inc.). The column was equilibrated with 0.2 mM Tris chloride, 5 mM 2-mercaptoethanol, and 1 mM $MgSO_4$. The enzyme was applied to the column, and the column was then eluted with the same buffer used to equilibrate it. Fractions of 200 drops each were collected. The enzyme eluted as one peak. All fractions containing rubber polymerase activity were pooled. Sodium dodecyl sulfate polyacrylamide gel electrophoresis of the pooled fractions indicated that the enzyme had been purified to near homogeneity. The pooled fractions generally contained approximately 10 mg of protein as analyzed by spectrophotometric techniques.

EXAMPLE V

Use of Substantially Purified Rubber Polymerase to Synthesize High Molecular Weight Natural Rubber Substantially purified rubber polymerase produced as in Example IV was used in the synthesis of high molecular weight natural rubber as follows:

In a test tube, 5 parts 2 M Tris chloride (pH 8.0), 1 part 0.65 M magnesium chloride, 2 parts 0.225 M dipotassium EDTA, 1 part 0.2 M glutathione, 1 part 1.5 mM DMAPP, 1 part 6 mM IPP, and 19 parts of a suspension of washed Ficus rubber particles (0.5% weight/volume rubber) were added. The reaction was initiated by the addition of 20 parts of substantially pure rubber polymerase (0.2 mg/ml). The mixture was incubated for 4 hours at 30° C.

The reaction was terminated by the stepwise addition 100 parts of 0.1 M dipotassium EDTA and 4,000 parts of 2% (w/v) trichloroacetic acid in methanol. The rubber was precipitated by this treatment and was isolated by centrifugation at 2,000 rpm for 10 minutes in a Sorvall GLC-4 centrifuge.

EXAMPLE VI

Preparation of Isopentenyl Pyrophosphate

IPP was prepared by the pyrophosphorylation of isopentenol and purified by crystallization.

To 15.12 ml (12.9 g, 150 mM) of isopentenol was added 90 ml (130 g, 900 mM) of trichloroacetonitrile in a flask fitted with a stirrer and dropping funnel. Bis-(triethylammonium) phosphate (104 g, 36 mM), dissolved by heating in 5 ml of acetonitrile, was then introduced through the dropping funnel over a period of 5½ hours, the reaction mixture being kept at room temperature and stirred continuously. After standing overnight at room temperature, 333 ml of 0.4 N aqueous ammonia and 700 ml of ether were added to the reaction mixture in a separatory funnel, and the phosphates were extracted into the aqueous phase. The extraction with 333 ml of 0.4 N aqueous ammonia was repeated twice more. The combined aqueous phases were extracted three times with 500 ml of ether and then concentrated on a rotary evaporator at 55° C. to approximately 200 ml. Cyclohexylamine (50 ml, 437 mM) was then added and the concentration continued to approximately 100 ml when crystals of the dicyclohexylammonium salt of isopentenyl monophosphate appeared. After standing overnight at 4° C., 7.6 g of crystalline monophosphate were collected.

The mother liquor was treated with 100 ml of concentrated aqueous ammonia and extracted twice with 2 volumes of ether (350 ml). After removal of ether, 500 ml of 1 M LiCl were added, and the solution was concentrated to approximately 500 ml when a precipitate of the lithium salt of isopentenyl pyrophosphate appeared. After standing at 4° C. for 24 hours, the precipitate was collected, washed with ice-cold water, then acetone and ether, and dried in an oven at 70° C. overnight. The yield was 8 g.

The lithium salt of isopentenyl pyrophosphate (8 g, 30 mM) was stirred with 50 ml water and weakly acidified with 50% acetic acid for removal of carbonate present, adjusted to pH 8 with 2 N NaOH and mixed dropwise with a solution of 16.45 g (64 mM) $Ba(C_2H_3O_2)_2$ in 48 ml water, whereby the poorly soluble amorphous barium isopentenyl pyrophosphate was precipitated. It was centrifuged and washed with 5 ml water 5 times, then with ethanol, acetone, and ether. The yield was 11.55 g.

Barium isopentenyl pyrophosphate (11.55 g) was suspended in 150 ml water and treated with 60 g Dowex 50 (H+ form), ion exchange resin at 0° C. for 1½ hours under magnetic stirring and at 4° C. overnight. The removal of barium was followed through spot testing with dilute $H_2SO_4$(1 N). The ion exchange resin was filtered and washed with deionized water until there was no barium in solution. The aqueous solution was neutralized with concentrated ammonia and concentrated in a rotary evaporator to near dryness to produce a yellowish syrup. The yellowish syrup was washed with acetone and then ether. The yield was 5.5 g. The IPP structure was confirmed by both proton and phosphorus-31 NMR and gas chromatography-mass spectrometry.

What is claimed is:

1. A process for stabilizing natural rubber latex which comprises adding to said natural rubber latex a stabilizing composition comprising a polyhydroxy compound, an antimicrobial agent, and a buffer.

2. The process of claim 1 wherein said stabilizing composition further comprises a sulfhydryl compound.

3. The process of claim 1 wherein said stabilizing composition is a solution.

4. The process of claim 3 wherein said solution has a pH from about 7 to about 12.

5. The process of claim 3 wherein from about 1 to about 10 volumes of said stabilizing solution are added to approximately 1 volume of said natural rubber latex.

6. The process of claim 3 wherein approximately two volumes of said stabilizing solution are added to approximately one volume of said natural rubber latex.

7. The process of claim 3 wherein said stabilizing solution comprises approximately 50% weight/volume glycerol, approximately 0.3% weight/volume sodium azide, and approximately 0.1 M sodium bicarbonate.

* * * * *